United States Patent [19]

Dürr et al.

[11] Patent Number: 5,098,295
[45] Date of Patent: Mar. 24, 1992

[54] PLUG CONNECTION

[75] Inventors: Walter Dürr, Remchingen; Axel Kirsch, Talstr. 23, 7024 Filderstadt, both of Fed. Rep. of Germany

[73] Assignees: Axel Kirsch; Eberle Medizintechnische Elemente GmbH, Fed. Rep. of Germany

[21] Appl. No.: 480,066

[22] Filed: Feb. 14, 1990

[30] Foreign Application Priority Data

Feb. 14, 1989 [DE] Fed. Rep. of Germany ....... 3904340

[51] Int. Cl.$^5$ .......................................... A61C 13/225
[52] U.S. Cl. .................................... 433/172; 433/169
[58] Field of Search ................ 433/169, 172, 193, 194

[56] References Cited

U.S. PATENT DOCUMENTS

| 4,290,755 | 9/1981 | Scott | 433/173 |
| 4,318,696 | 3/1982 | Kasama et al. | 433/169 |
| 4,382,791 | 5/1983 | Misch | 433/172 |
| 4,447,210 | 5/1984 | Hidaka et al. | 433/169 |
| 4,681,542 | 7/1987 | Baum | 433/172 |
| 4,793,808 | 12/1988 | Kirsch | 433/173 |

FOREIGN PATENT DOCUMENTS

| 7130368 | 8/1971 | Fed. Rep. of Germany . |
| 2945489 | 5/1981 | Fed. Rep. of Germany ...... 433/172 |
| 3706816 | 9/1987 | Fed. Rep. of Germany ...... 433/172 |
| 8708671 | 1/1988 | Fed. Rep. of Germany . |
| 0641037 | 2/1984 | Switzerland ........................ 433/172 |

Primary Examiner—Gene Mancene
Assistant Examiner—Adriene B. Lepiane
Attorney, Agent, or Firm—Hill, Van Santen, Steadman & Simpson

[57] ABSTRACT

A plug connection for the detachable fitting of a prosthesis structure such as a tooth on a tooth peg or post characterized by a plug part provided on the post having a cylindrical base with a tip having a portion of a larger diameter than the base and having a circumferential conical surface extending to a tip, a socket part having a cavity for receiving the plug part and containing a clamping ring for engaging the shoulder formed at the portion and base and supporting a bearing ring in the cavity of an elastic plastic material for relieving impact stresses occurring substantially in a direction of a longitudinal axis of symmetry of the post.

14 Claims, 1 Drawing Sheet

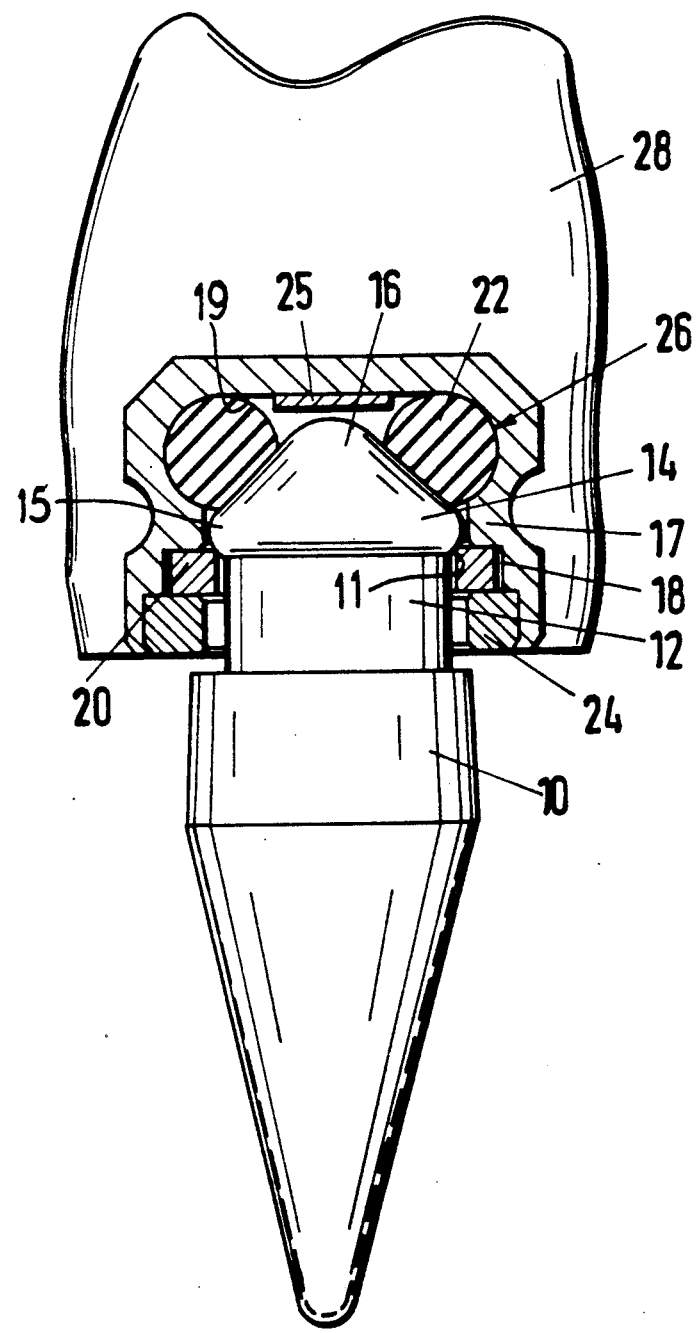

PLUG CONNECTION

BACKGROUND OF THE INVENTION

The present invention relates to a plug connection for the detachable fitting of a prosthesis structure or the like to a fixing head of a peg, tooth post or the like. The peg or tooth post is provided with a plug part on a fixed head having an all-around constriction in a plane substantially perpendicular to the longitudinal axis of symmetry of the fixing head, a socket part carrying the prosthesis structure and having elastic clamping ring inserted on the head with the ring engaging behind a construction of the plug part to form a positive connection between the plug part and socket part. The socket part is thus elastically mounted with respect to the plug part with regard to impact stresses occurring substantially in the direction of longitudinal axis of symmetry of the fixing head.

In a known plug connection of this type, the plug part connected to the fixing head of the peg or tooth post or the like is substantially spherically constructed. A large diameter area of the sphere is engaged behind in the vicinity of the constriction facing the fixing head by a clamping ring constructed as an O-ring made from a relative flexible plastic and/or rubber material. The clamping ring simultaneously ensures the elastic mounting of the socket part and therefore the prosthesis structure in the direction of longitudinal axis of symmetry of the fixing head. The front inner face of the socket part, which is substantially at right angles to the longitudinal axis of symmetry of the plug connection, is kept spaced from the end of the plug part remote from the fixing head so that in the case of impact stresses or the like, even in the case of a chewing movement, the forces acting in the direction of longitudinal axis of symmetry do not lead to the pressing of the socket part and therefore, the prosthesis structure against the plug part and consequently onto the fixing head of the peg or tooth post. Thus, in a desirable manner, it is ensured that all of the forces exerted on the prosthesis structure are not deflected to the peg or the tooth post and instead, following a movement in the direction of longitudinal axis of symmetry, for example, 0.5 mm, the dental prosthesis or the like is supported on the jaw ridge. However, as a result of the "floating" mounting of the socket part due to the O-ring fulfilling both the clamping and holding function, as well as the resilient bearing function, lateral movements occur and after a short time lead to the destruction of the O-ring. Thus, the known plug connection suffers from the disadvantage that it wears after a relative short time so that frequently after a few weeks the O-ring or, if as is usually the case the prosthesis is carried by several such plug connections, the O-rings have to be replaced.

Another plug confection for prosthesis structure is realized in that the fixing head of the peg or tooth post or the like is provided with a "socket" in the form of a hemispherical shell made from polyoxymethylene or the like and is provided with an undercut with which it is engaged in a snapping fit on a spherical "plug" of the prosthesis structure. However, this plug connection suffers from the disadvantage that due to the necessarily relatively rigid material of the ½ or ¾ spherical shell of the material such as polyoxymethylene, the vertical elasticity is not adequate. Thus, compressive stresses of the prosthesis structure cannot be supported on the jaw ridge and are instead completely transferred to the peg or tooth post or the like with all the disadvantages consequently resulting therefrom. Another disadvantage of this plug connection is that between the spherical head and the spherical shell, deposits can occur, for example, in the form of fine-grained lime which will cause a rapid wear of the spherical head of the plug connection.

SUMMARY OF THE INVENTION

The object of the present invention is to create a plug connection of the aforementioned type which, in the case of a high elasticity of the support which can be obtained, has a much better resistance to wear.

According to the invention, the problem is solved in that the plug part has a cylindrical base connected to the peg or tooth post and a mushroom-shaped top connected thereto. The mushroom-shaped top has a portion with a maximum external diameter which is close to the end of the base remote from the tooth post or peg and the maximum diameter exceeds the external diameter of the base to form an annular shoulder. The mushroom-shaped top has a circumferential surface extending conically from the portion of the maximum diameter to a flattened top or tip. A socket part is provided in the vicinity of the constriction with a ring recess for the partial reception of an elastic clamping ring and a bearing ring made from elastic plastic or rubber material is provided between the conical circumferential surface of the top and the interior of the socket part.

The bearing ring can be constructed as an O-ring.

The clamping ring can be made from a plastic material, for example, polyoxymethylene.

Another embodiment of the invention proposes that the clamping ring material is much more rigid than that of the bearing ring. The invention optionally also proposes that the clamping ring material has substantially a rectangular cross-section and that the clamping ring can be secured by a holding ring in the ring recess of the socket part.

Another embodiment of the invention is characterized in that a dampening layer is provided between the top tip of the plug part at the inner end face of the socket part in the direction of longitudinal axis of symmetry. The dampening layer can be applied either to the top tip of the mushroom-shaped part or to the inner end surface of the socket part.

The invention can also be characterized in that the socket part has a circular groove for the partial reception of the bearing ring.

The invention is based on the surprising finding that it is possible to overcome the disadvantages of the prior art by the fact that the function of the holding of the socket part on the plug part and the elastic supporting of the socket part combined in the prior art in a single element namely the clamping ring is now distributed between two separate elements. These are constituted as the clamping ring preferably made from a relatively rigid plastic material such as polyoxymethylene whose function is solely to hold the socket part detachably on the plug part. The bearing ring is made from a relatively soft or flexible material whose only function is to support the socket part resiliently with respect to the plug part and therefore the fixing head of the peg or tooth post or the like. If, as in the case of the preferred embodiment of the invention, the clamping ring is made with a rectangular cross-section, is partially located in a corresponding recess of a socket part and is held by a holding ring, it fulfills the further function of sealing with respect to the oral cavity the inner region of the socket part in which is arranged the sensitive bearing ring which is made from a relative soft elastic material. Thus, deposits, which might have a negative influence on the bearing ring, cannot penetrate into a gap between the socket part and the conical circumferential surface of the plug part.

Other features and advantages of the invention can be gathered from the following description of the preferred embodiment, the drawing and claims.

BRIEF DESCRIPTION OF THE DRAWINGS

The FIGURE is a longitudinal cross-section with portions in elevation for purposes of illustration of the plug connection in accordance with the present invention.

DESCRIPTION OF THE PREFERRED EMBODIMENTS

Principles of the present invention are particularly useful when incorporated in a plug connection illustrated in the FIGURE between a socket part 17 which supports a prosthesis structure 28 such as a tooth and a peg, pin, or post 10.

The peg, pin or post 10, which is made of titanium, has on its upper end a plug part formed by a substantially cylindrical base 12 and a substantially mushroom-shaped top 14. The top 14 has a portion 15 with the greatest diameter which is close to an upper end of the base 12 and has an outside diameter greater than the diameter of the base 12 to form a shoulder 11. The mushroom-shaped top 14 above the portion 15 has a substantially conical configuration extending to a tip or top 16.

The socket part 17, which is also made of titanium, is provided with a ring recess 18 which partly receives a polyoxymethylene clamping ring 20 which will engage behind the shoulder 11 which is formed by a constriction between the base 12 and the maximum diameter portion 15 of the top 14 of the plug part 12. A bearing ring 22, which is made from a relatively soft or flexible silicon rubber and is constructed as an O-ring, is positioned between the conical surface of the top 14 and an inner end face or surface 19 of the socket part 17. As illustrated, preferably the socket part 17 has a circular or annular groove 26 partly receiving this bearing ring 22.

As mentioned, the clamping ring 20 is inserted in the still open recess 18 and then a holding ring 24 is inserted and fixed, for example, by beading, crimping, or swaging. Also, a dampening layer 25 in the form of a small silicon rubber plate is disposed between the inner end face 19 of the socket part and a top tip 16 of the plug part. As illustrated, this is stuck on the inner face 19 of the socket part, however, it could be applied on the tip 16.

The plug connection, according to the invention, functions as follows. Following the insertion of the peg, pin, or post 10 which could also be an implant post or a fixing head or the like fitted to a tooth stump, the socket part connected to the prosthesis structure 28 is provided. The loose elements, namely the bearing ring 22 and the clamping ring 20, are already assembled in the socket part with the holding ring 24 holding the clamping ring 20. The socket part is then forced in the direction of longitudinal axis of symmetry onto the top 14. The clamping ring 20 is slightly widened and finally snaps behind the maximum diameter portion 15 of the mushroom-shaped top 14 of the part 12. In this position, the tip 16 has a distance of approximately 1 mm from the end face 19 of the socket part 17. In the case of compressive stresses resulting from chewing movements, for example, it is possible to have a significant relative movement of up to 1 mm cushioned by the elastic bearing ring 22 in the direction of the longitudinal axis of symmetry between the socket part 17 and the base 12 and therefore, the post 10. Simultaneously, the bearing in the direction at right angles to the longitudinal axis of symmetry is extremely precise and not floating which ensures a satisfactory seating of the prosthesis structure or The like.

While a preferred embodiment has been shown, modifications and changes may become apparent to those skilled in the art which shall fall within the spirit and scope of the invention. It is intended that such modifications and changes be covered by the attached claims.

We claim:

1. A plug connection for the detachable fitting of a prosthesis structure or the like to a fixing head of a post, said plug connection comprising a post having a plug part having a longitudinal axis of symmetry and being formed by a cylindrical base connected to an upper end of the post and a mushroom-shaped top being connected to said base, said mushroom-shaped top having a portion with a maximum diameter greater than the external diameter of the base, said portion being adjacent the base to form a constriction having a shoulder, said mushroom-shaped top extending from said portion of a maximum diameter with a circumferential continuous conical surface extending to a flattened tip; a socket part for supporting the prosthesis structure, said socket part having a cavity with an inner end surface essentially perpendicular to said longitudinal axis with a wall portion extending therefrom essentially concentrically to said longitudinal axis, said wall portion having a ring recess spaced from said end surface and opening into the cavity in the vicinity of said construction, and an elastic clamping ring of an elastic material received in said recess and said constriction; and means for cushioning the socket part on said plug part in both a longitudinal direction and a direction at right angles thereto, said means comprising a bearing ring being an O-ring of an elastic plastic material, the material of the clamping ring being much more rigid than the material of the O-ring, said O-ring being disposed in a circular groove provided in said wall portion of said cavity adjacent said inner end surface and in contact with the end surface so that with a socket part inserted on the plug part with the clamping ring engaging the shoulder said bearing ring is positioned between the inner end surface of the cavity of the socket part and the circumferential continuous conical surface of the top to cushion forces applies to the prosthesis substantially in both the direction of said longitudinal axis of symmetry of the plug part and in the direction at right angles thereto.

2. A plug connection according to claim 1, wherein the plastic material of the clamping ring is polyoxymethylene.

3. A plug connection according to claim 2, wherein the material of the clamping ring has a substantially rectangular cross-section.

4. A plug connection according to claim 1, wherein the clamping ring has a substantially rectangular cross-section.

5. A plug connection according to claim 1, wherein a dampening layer is positioned between the tip of the plug part and the inner end surface of the socket part in the direction of the longitudinal axis of symmetry.

6. A plug connection according to claim 5, wherein the dampening layer is applied to the tip.

7. A plug connection according to claim 5, wherein the dampening layer is applied to the inner end surface of the socket part.

8. A plug connection for the detachable fitting of a prosthesis structure onto a post or the like, said plug connection comprising a post having a plug part with a longitudinal axis of symmetry, a socket for supporting the prosthesis and having a cavity for receiving said plug part, and means received in said cavity for cushioning both longitudinal stresses applied in the direction of said longitudinal axis of symmetry of said post and stresses extending transverse to said axis, said plug part being formed by a cylindrical base and a mushroom-shaped top having an annular portion of a maximum outer diameter greater than the diameter of the cylindrical base adjacent the base to form an engagement shoulder, said mushroom-shaped top having a conical continuous surface extending from said maximum portion to a tip, said cavity having an inner end surface extending essentially perpendicular to said longitudinal axis and a wall portion being essentially concentric to said longitudinal axis with a ring recess being spaced from the end surface and opening into the cavity in the vicinity of the shoulder for receiving an elastic clamping ring, said means for resilient transfer comprising a bearing ring of elastic plastic material disposed in a circular groove provided in said wall portion of the cavity adjacent the inner end surface, said bearing ring being constructed as an O-ring and being engaged by the conical continuous surface of the top as the clamping ring engages the shoulder to hold the socket on said plug part, said clamping ring and shoulder coacting to form means for sealing the interior of the cavity and the bearing ring from the outside, said clamping ring being of a material which is much more rigid than the material of the O-ring.

9. A plug connection according to claim 8, wherein said clamping ring has a rectangular cross-section.

10. A plug connection according to claim 9, wherein the material of the clamping ring is polyoxymethylene.

11. A plug connection according to claim 8 which includes a holding ring received in the ring recess to hold the clamping ring therein.

12. A plug connection according to claim 8 which includes a dampening layer positioned between the inner end surface of the cavity of the socket part and the tip of the plug part.

13. A plug connection according to claim 12, wherein said dampening layer is applied to the inner end surface of the cavity of the socket part.

14. A plug connection for the detachable fitting of a prosthesis structure or the like to a fixing head of a post, said plug connection comprising a post having a plug part formed by a cylindrical base connected to an upper end of the post and a mushroom-shaped top being connected to said base, said mushroom-shaped top having a portion with a maximum diameter greater than the external diameter of the base, said portion being adjacent the base to form a constriction having a shoulder, said mushroom-shaped top extending from said portion of a maximum diameter with a circumferential conical surface extending to a flattened tip; a socket part for supporting the prosthesis structure, said socket part having a cavity with a ring recess, an elastic clamping ring received in said recess and a holding ring in the recess to secure the clamping ring therein; and a bearing ring of an elastic plastic material being disposed in said cavity so that with the socket part inserted on the plug part with the clamping ring engaging the shoulder, said bearing ring is positioned between an inner surface of the cavity of the socket part and the circumferential conical surface of the top to cushion forces applied to the prosthesis substantially in the direction of a longitudinal axis of symmetry of the plug part.

* * * * *